US011814416B2

(12) United States Patent
Li et al.

(10) Patent No.: US 11,814,416 B2
(45) Date of Patent: Nov. 14, 2023

(54) POLYPEPTIDE CAPABLE OF PASSING THROUGH BLOOD-BRAIN BARRIER

(71) Applicant: SHENZHEN RUIJIAN BIOSCIENCE TECHNOLOGY LIMITED COMPANY, Guangdong (CN)

(72) Inventors: Shupeng Li, Guangdong (CN); Qiang Zhou, Guangdong (CN)

(73) Assignee: SHENZHEN RUIJIAN BIOSCIENCE TECHNOLOGY LIMITED COMPANY, Guangdong (CN)

( * ) Notice: Subject to any disclaimer, the term of this patent is extended or adjusted under 35 U.S.C. 154(b) by 242 days.

(21) Appl. No.: 17/277,552

(22) PCT Filed: Dec. 27, 2018

(86) PCT No.: PCT/CN2018/124253
§ 371 (c)(1),
(2) Date: Mar. 18, 2021

(87) PCT Pub. No.: WO2020/056987
PCT Pub. Date: Mar. 26, 2020

(65) Prior Publication Data

US 2022/0112250 A1 Apr. 14, 2022

(30) Foreign Application Priority Data

Sep. 18, 2018 (CN) ........................ 201811086051.5

(51) Int. Cl.

| | |
|---|---|
| ***C07K 14/435*** | (2006.01) |
| ***A61K 47/65*** | (2017.01) |
| ***A61P 29/00*** | (2006.01) |
| ***A61K 38/00*** | (2006.01) |

(52) U.S. Cl.
CPC ........ *C07K 14/43504* (2013.01); *A61K 47/65* (2017.08); *A61P 29/00* (2018.01); *A61K 38/00* (2013.01)

(58) Field of Classification Search
CPC .......... C07K 14/43504; C07K 2319/10; C07K 2319/03; A61K 47/65; A61K 38/00; A61P 29/00
See application file for complete search history.

(56) References Cited

U.S. PATENT DOCUMENTS 8,288,345 B2 * 10/2012 Belmares ................ C07K 7/06 514/17.4
9,061,070 B2 * 6/2015 Belmares ................ A61P 25/00
2008/0274977 A1 * 11/2008 Belmares ................ A61P 43/00 514/17.7
2013/0172230 A1 * 7/2013 Belmares .................. A61P 9/10 530/397
2015/0119340 A1 * 4/2015 Kim ....................... C12N 15/87 514/21.3

FOREIGN PATENT DOCUMENTS

| | | | | |
|---|---|---|---|---|
| CN | 108992661 A | | 12/2018 | |
| EP | 2559441 A2 | | 2/2013 | |
| EP | 2 876 164 | * | 5/2015 | ............. C12N 15/87 |
| EP | 2876164 A2 | | 5/2015 | |

OTHER PUBLICATIONS

Liu et al. Translation from Chinese to English. Research on the Relationship Between Refolding and Bioactivity of a New Type of Conotoxin SO3. Letters in Biotechnology. vol. 12, No. 3, pp. 181-183. (Year: 2001).*
Liu, F-Y. et al. “Research on the relationship between refolding and bioactivity of the new type of conotoxin SO3”, in Letters in Biotechnology, Aug. 2001, pp. 181-183, vol. 12, No. 3.
International Search Report for related International Application No. PCT/CN2018/124253, dated May 29, 2019; English translation provided (6 pages).
Anand, P. et al. “Tailored delivery of analgesic ziconotide across a blood brain barrier model using viral nanocontainers” in Scientific Reports, Aug. 3, 2015, pp. 1-10.

* cited by examiner

*Primary Examiner* — Marcela M Cordero Garcia
(74) *Attorney, Agent, or Firm* — Procopio, Cory, Hargreaves & Savitch LLP

(57) ABSTRACT

The present invention provides a polypeptide capable of crossing the blood-brain barrier. In the present invention, C-terminal of the ziconotide is linked to N-terminal of a cell membrane penetrating peptide via one glycine to obtain a polypeptide capable of crossing the blood-brain barrier. The polypeptide of the present invention is suitable for intravenous, intraperitoneal or nasal administration with convenient operation and low clinical risk. It has a long pharmacological effect in vivo, excellent analgesic effect, and slight peptide side effect after intravenous, intraperitoneal or nasal administration, and is suitable for large-scale clinical applications. The polypeptide of the invention has the advantages of simple preparation, controllable preparation process and quality during the preparation, and is suitable for large-scale industrial production.

13 Claims, 11 Drawing Sheets

Specification includes a Sequence Listing.

G

| Peptides | MVIIA | MVIIA-a | MVIIA-b | MVIIA-c | MVIIA-d |
|---|---|---|---|---|---|
| IC50 (μM) | 0.0436 | 0.4127 | 0.3788 | 0.2367 | 0.3446 |
| 95% Confidence Intervals (μM) | (0.0391, 0.0487) | (0.3640, 0.4680) | (0.3533, 0.4063) | (0.2238, 0.2504) | (0.3167, 0.3748) |

\# compared with the saline group
* compared with the MVIIA group
& compared with the MVIIA-C group

POLYPEPTIDE CAPABLE OF PASSING THROUGH BLOOD-BRAIN BARRIER

CROSS-REFERENCE TO RELATED APPLICATIONS

This application is a U.S. National Stage entry of PCT Application No: PCT/CN2018/124253 filed Dec. 27, 2018, which claims priority to Chinese Patent Application No. 201811086051.5, filed on Sep. 18, 2018, the contents of which are incorporated herein by reference.

FIELD OF THE INVENTION

The present invention belongs to the technical field of polypeptide medicament, and particularly relates to a fusion polypeptide of ziconotide.

BACKGROUND OF THE INVENTION

Ziconotide (with the trade name of Prialt™, Elan Pharmaceuticals) was the first conotoxin drug approved by the Food and Drug Administration (FDA) in 2004. It is the first-line drug for complex analgesia in the subarachnoid space (intrathecal) with the target site at the N type voltage-gated calcium channel. Ziconotide is a synthetic compound derived from ω-MVIIA, a hydrophilic polypeptide of the venom peptides from the cone snail that is a Pacific fish-eating snail. It is the first new type of non-morphinoidanalgesic used in clinical practice, with a molecular formula of $C_{102}H_{172}N_{36}O_{32}S_7$ and a structural formula: H-Cys-Lys-Gly-Lys-Gly-Ala-Lys-Cys-Ser-Arg-Leu-Met-Tyr-Asp-Cys-Cys-Thr-Gly-Ser-Cys-Ar g-Ser-Gly-Lys-Cys-$NH_2$ (SEQ ID NO:1).

Ziconotide can be used clinically to treat postherpetic neuralgia, phantom limb pain, AIDS-related neuropathic pain, refractory cancer pain, postoperative pain, pain that is intolerable or refuses other therapies such as systemic analgesic drug, adjuvant therapy, alleviation, intrathecal injection of opioids with no response, etc. The therapeutic mechanism of ziconotide is through its ability to bind N-type calcium channel receptors, which is different from that of salicylate, NSAIDs and local anesthetics mainly through peripheral nerves/nociceptors, and opioids and general anesthetics mainly acting on the brain level to eliminate pain and consciousness. The N-type calcium channel receptors are located on the main nociceptive A-δ and C-slow fiber pain fibers (nociceptors) in Rexed's laminae I and II on the back surface of the spinal cord. Ziconotide can relieve pain that has no response to other therapies including intrathecal injection of morphine, and will not develop tolerance and addiction after prolonged use. Its application is indicated for the treatment of chronic pain related to trauma, tumor, neuralgia and the like, especially with unique advantages in treating patients with refractory pain that are insensitive to opioids or who are intolerant of opioids. However, due to the inability to cross the blood-brain barrier, ziconotide is currently only infused by using intrathecal catheterization with the cannula and infusion pump buried under the skin, which requires surgery and is inconvenient for clinical use. It is currently used only for the long-term, permanent treatment of chronic pain that is resistant to existing analgesics. Such mode of administration greatly limits the clinical application of the inherent advantages of the drug.

The blood-brain barrier (BBB), a complex cell system that exists between the brain tissue and the blood, can control the transport of substances from both sides of blood and brain, and therefore ensure the stability of the internal environment of the central nervous system: useful substances in the blood are transported into brain according to the needs of the body by interacting with various receptors on the microvascular endothelial cell membrane so as to play a role; while some toxic and harmful substances are shielded from the brain tissue by the barrier to prevent damage to the brain. Such special protective effect of the blood-brain barrier (BBB) makes it difficult for most drugs to enter the brain, which causes problems in the treatment and administration for the central nervous system disease.

Cell penetrating peptides (CPP) are short peptides (generally less than 35 amino acid residues) that can enter cells by crossing biological membranes. They were discovered in 1988, specifically, some scholars discovered that the trans-activator protein Tat of HIV-1 could be transduced into cells across the membrane, and then it was discovered that the *drosophila* transcription protein also had similar properties. Thereafter, many other CPPs had been discovered one after another. CPPs showed diversity in relative molecular mass, amino acid composition, and amino acid sequence, with differences in the numbers and types of the contained amino acids, as well as the polarity and charge quantity, but they have some common features, for example, entering cells by crossing the cell membrane without causing significant destroy or damage to the membrane under a lower concentration condition; not only having the ability to penetrate the membrane itself, but also mediating various substances, including small molecules, nucleic acids, protein polypeptides, nanoparticles and the like, into cells; having high efficiency and low toxicity. In recent years, studies have found that the use of cell penetrating peptides to bind to drug molecules can achieve the effect of crossing the blood-brain barrier, which brings a new direction for central nervous system drug delivery.

Currently, there are technical methods for helping conotoxin to cross the blood-brain barrier by using cell penetrating peptides in the prior art. For example, ziconotide is packaged in a viral particle, and a TAT polypeptide is attached to the surface of the viral particle, which can deliver ziconotide across the blood-brain barrier. However, such method comprise a complicated preparation process and the virus packaging process cannot be well quality controlled, thus it is difficult to be applied on a large scale in industry. In another example, the TAT peptide is linked to the N-terminal of the conotoxin with two GG as a linker to prepare a fusion polypeptide that is suitable for intravenous administration due to its blood-brain barrier penetration. However, the analgesic effect and existence time in vivo of such N-terminally linked fusion polypeptide by intravenous injection cannot meet the requirements of clinical application, so it cannot be promoted on a large scale. Therefore, it is a problem that needs to be solved urgently to obtain an improved ziconotide that can cross the blood-brain barrier, overcome the shortcomings of intrathecal intubation, and can be used clinically on a large scale.

SUMMARY OF THE INVENTION

One of the objectives of the present invention is to provide a polypeptide with blood-brain barrier penetrability. Through long-term research, the inventor have discovered that a fusion peptide with blood-brain barrier penetration can be obtained by linking C-terminal of ziconotide with N-terminal of a membrane penetrating peptide. It can overcome the shortcomings of the prior art, is suitable for intravenous, abdominal or nasal administration, has good analgesic effect in vivo with longer effect time, and can be used clinically on a large scale.

Specifically, the technical solutions to achieve above objectives are as follows.

A polypeptide, consisting of ziconotide and a cell membrane penetrating peptide. Preferably, the polypeptide is consisted of ziconotide linked to the cell membrane penetrating peptide via C-terminal, or C-terminal of the ziconotide is linked to N-terminal of a cell membrane penetrating peptide via a linker, preferably, the linker is one glycine.

Further, the ziconotide has amino acids of CKGKGAKCSRLMYDCCTGSCRSGKC (shown in SEQ ID NO.1), or the ziconotide in the fusion polypeptide is a variant of the amino acids of CKGKGAKCSRLMYDCCTGSCRSGKC (shown in SEQ ID NO.1) with less than 10, less than 8, less than 6, less than 4, 2 or 1 amino acid deletions, mutations or insertions.

Further, the cell membrane penetrating peptide is Penetratin, TAT peptide, Pep-1 peptide, $S4_{13}$-PV, Magainin 2 or Buforin 2.

Wherein the TAT peptide is derived from HIV-1 transactivator protein Tat, which can transduce into cells across the membrane. The TAT peptide has amino acids of YGRKKRRQRRR (shown in SEQ ID NO.2), or the TAT peptide in the fusion polypeptide is a variant of the amino acids of YGRKKRRQRRR (shown in SEQ ID NO.2) with less than 10, less than 8, less than 6, less than 4, 2 or 1 amino acid deletions, mutations or insertions, or a peptidomimetic thereof.

Preferably, the above polypeptide or fusion polypeptide or improved ziconotide has amino acids of CKGKGAKCSRLMYDCCTGSCRSGKCGYGRKKRRQRRR (shown in SEQ ID NO.5), or is a variant with less than 10, less than 8, less than 6, less than 4, 2 or 1 amino acid deletions, mutations or insertions, or a peptidomimetic thereof.

The peptidomimetic refers to a synthetic chemical compound that has substantially identical structural and/or functional characteristics to a peptide composed of natural amino acids. The peptidomimetic may completely comprise synthetic non-natural analogs of amino acids, or a chimeric molecule of partial natural peptide amino acids and partial non-natural amino acid analogs. The peptidomimetic may also incorporate any number of natural amino acid conservative substitution sites, as long as such substitution does not substantially change the structure and/or inhibitory activity or binding activity of the mimetic. Polypeptide mimetic components may contain any combination of non-natural structural components, which generally derive from 3 structural groups: a) a residue linking group linked by a non-natural amide bond ("peptide bond"); b) a non-natural residue that replaces a naturally occurring amino acid residue; or c) a residue that induces secondary structure simulation, that is, induces or stabilizes secondary structures such as β turn, γ turn, β sheet, a helix conformation, etc.

The second objective of the present invention is to provide a pharmaceutical composition or formulation, preferably a pharmaceutical formulation, further, the pharmaceutical composition or formulation/pharmaceutical formulation comprises the polypeptide of the present invention and/or an acceptable carrier.

The pharmaceutical composition or formulation/pharmaceutical formulation may comprise any dosage shown below in a unit dosage form (i.e., a dosage for single administration) to provide a pharmaceutical composition. It can be prepared by conventional methods such as mixing, dissolving, granulating, preparing lozenges, grinding, emulsifying, encapsulating, embedding or lyophilizing. One or more physiologically acceptable carriers, diluents, excipients or adjuvants that facilitate the processing of the active agent into a pharmaceutically acceptable formulation can be used to formulate the pharmaceutical composition or formulation/pharmaceutical formulation in a conventional manner. The appropriate formulation depends on the chosen route of administration.

The mode of administration can be parenteral, intravenous, oral, subcutaneous, intraarterial, intracranial, intrathecal, intraperitoneal, topical, intranasal or intramuscular administration. Intravenous administration or intraperitoneal injection is preferred. The pharmaceutical composition or formulation/pharmaceutical formulation for parenteral administration is preferably sterile and substantially isotonic. For injection, the active agent can be formulated in an aqueous solution, preferably a physiologically compatible buffer such as Hank's solution, Ringer's solution, or physiological saline or acetate buffer (to reduce discomfort at the injection site). The solution may contain a formulating agent such as suspending agent, stabilizer and/or dispersing agent.

The third objective of the present invention is to provide use of the polypeptide. The use is: for the preparation of a medicament, preferably, for the preparation of an analgesic, preferably, the analgesic acts on a calcium channel.

Further, the medicament can be used to treat pain and pain-related diseases, for example, diseases that can cause chronic pain include diabetes, arthritis (e.g., osteoarthritis, rheumatoid arthritis and juvenile chronic arthritis), cancer, or toxic effects from chemotherapy, fibromyalgia, shingles, irritable bowel syndrome, vascular problems or sickle cell disease.

Diseases related to occasional ordinary pain include polymyalgia rheumatica, hypothetical disease, depression, diabetes, pernicious anemia, sickle cell disease, and syphilis. Diseases related to neuropathic pain include neuralgia (e.g., trigeminal neuralgia, atypical facial pain, and herpes zoster neuralgia caused by herpes zoster or herpes), peripheral neuropathy, Charcot-Marie-Tooth disease, Friedreich's ataxia, diabetes (e.g., diabetic neuropathy), dietary defects (especially vitamin B-12), excessive alcohol use (alcoholic neuropathy), uremia (from kidney failure), cancer, AIDS, hepatitis, Colorado tick fever, diphtheria, Guerrilla-Barr syndrome, HIV infection that has not developed into AIDS, leprosy, Lyme disease, multiple nodular arteritis, rheumatoid arthritis, sarcoidosis, Sjogren's syndrome, syphilis, systemic lupus erythematosus, and exposure to toxic compounds.

Diseases related to inflammatory pain include: (A) arthritis diseases, such as rheumatoid arthritis; juvenile chronic arthritis; systemic lupus erythematosus (SLE); gouty arthritis; scleroderma; osteoarthritis; psoriatic arthritis; ankylosing spondylitis; Reiter's syndrome (reactive arthritis); adult Still's disease; arthritis from viral infections; arthritis from bacterial infections, for example, gonorrhea arthritis and non-gonorrhea bacterial arthritis (septic arthritis); tertiary Lyme disease; tuberculous arthritis; and arthritis from fungal infections, such as yeast disease; (B) autoimmune diseases, such as Guerrilla-Barr syndrome, Hashimoto's thyroiditis, pernicious anemia, Addison's disease, type I diabetes, systemic lupus erythematosus, dermatomyositis, Sjogren's syndrome, lupus erythematosus, multiple sclerosis, myasthenia gravis, Reiter's syndrome and Graves' disease; (C) connective tissue diseases, such as spondyloarthritis, dermatomyositis and fibromyalgia; (D) inflammation caused by injury; (E) infections, such as tuberculosis or interstitial keratitis; and (G) arthritis, such as bursitis or tendinitis. Types of headache include muscular/myogenic headache, vascular headache, traction or inflammatory headache, cluster headache, hormonal headache, rebound headache, or chronic sinusitis headache.

Somatic pain can be related to the following: excessive muscle contraction, repetitive motion diseases, muscle diseases such as polymyositis, dermatomyositis, lupus, fibromyalgia, polymyalgia rheumatica, as well as rhabdomyolysis, myalgia, infections such as muscle abscess, trichinosis, influenza, Lyme disease, malaria, Rocky Mountain spotted fever, avian flu, common cold, socially acquired pneumonia, meningitis, monkeypox, serious acute respiratory syndrome, toxic shock syndrome, trichinosis, typhoid fever, and upper respiratory tract infections. Visceral pain can be associated with diseases such as irritable bowel syndrome, chronic functional abdominal pain (CFAP), functional constipation, functional dyspepsia, non-cardiac chest pain (NCCP) and chronic abdominal pain, chronic gastroenteritis, e.g., gastritis, inflammatory bowel disease, such as Crohn's disease, ulcerative colitis, microscopic colitis, diverticulitis and gastroenteritis; interstitial cystitis; intestinal ischemia; cholecystitis; appendicitis; gastroesophageal reflux; ulcers, kidney stones, urinary tract infections, pancreatitis and hernias.

The fourth objective of the present invention is to provide a method for preparing the polypeptide of the present invention. Preferably, the polypeptide of the present invention can be prepared by chemical synthesis. Further preferably, the preparation is carried out by a solid-phase synthesis method or a recombinant expression method, and further, the polypeptide of the present invention is prepared by the F-moc automatic solid-phase synthesis method.

Compared with the prior art, the present invention has the beneficial effects that an improved ziconotide obtained by linking C-terminal of ziconotide with a cell membrane penetrating peptide overcomes defects such as the inability of ziconotide to cross the blood-brain barrier, inability for intramuscular injection, and high surgical and infection risk from mainly intraventricular and spinal canal administration. The polypeptide of the present invention can cross the blood-brain barrier, and is suitable for intravenous, intraperitoneal or nasal administration with convenient operation and low clinical risk. It has a long pharmacological effect in vivo, excellent analgesic effect, and slight side effect after intravenous, intraperitoneal or nasal administration, and thus is suitable for large-scale clinical applications. Moreover, the polypeptide of the invention has the advantages of simple preparation, controllable preparation process and quality during the preparation, and is suitable for large-scale industrial production.

BRIEF DESCRIPTION OF THE DRAWINGS

FIG. 5A-FIG. 5C showed in vivo antinociceptive effects after tail intravenous administration of MVIIA-a, b, d polypeptides. Antinociceptive effects were expressed as a percentage of the maximum possible effect (% MPE). Data were presented as mean±S.E.M., with 8-10 mice in each group. *$p<0.05$, $p<0.01$ and *$p<0.001$ indicated comparison with the normal saline group;

DETAILED DESCRIPTION OF THE INVENTION

Figure 1:
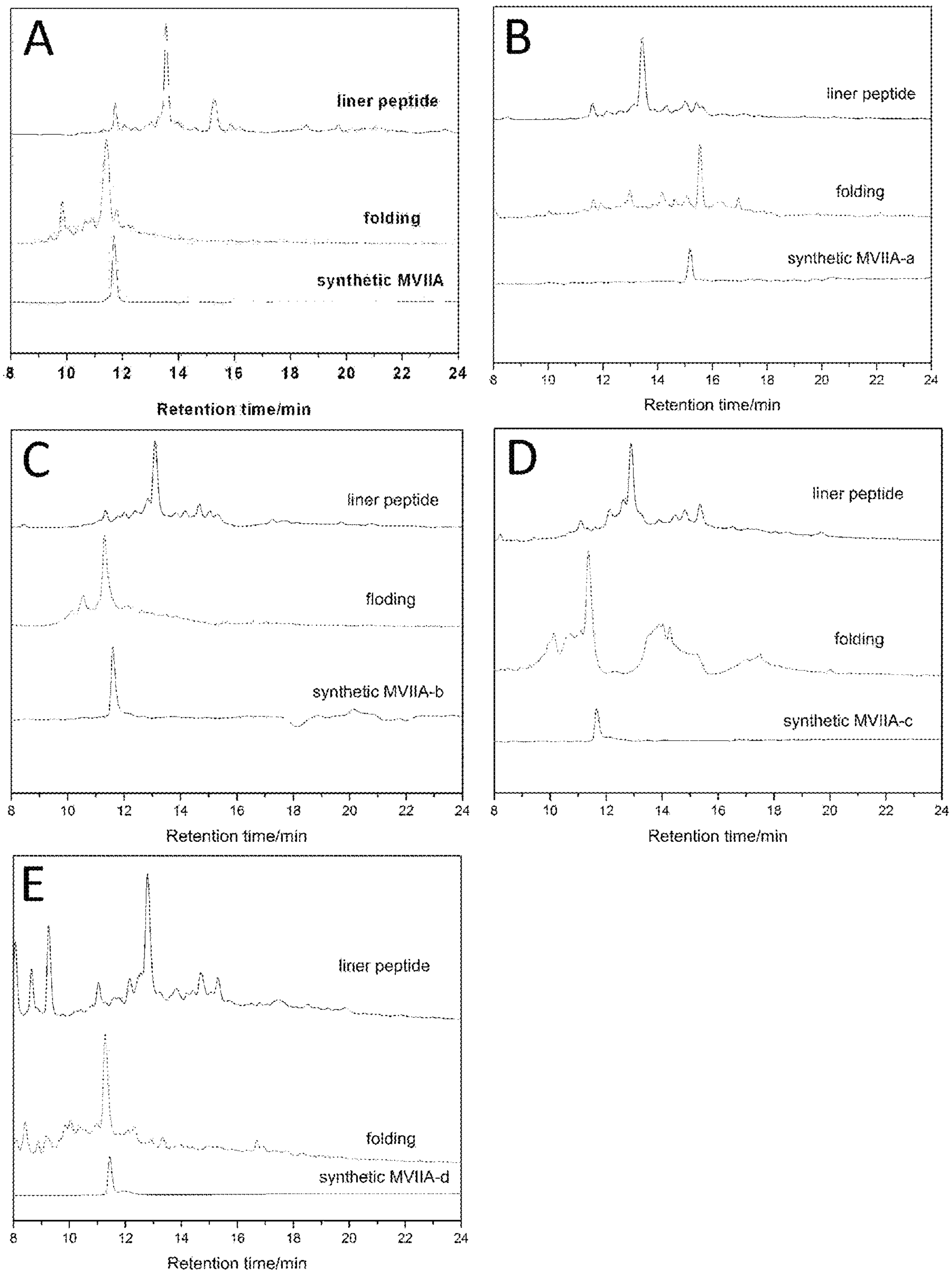
FIG. 1: HPLC analysis profiles of one-step oxidation folding of MVIIA and MVIIA-a, b, c, d.

In order to overcome the shortcomings of ziconotide in the prior art, the inventor have discovered through long-term research that an improved ziconotide fusion peptide obtained by linking C-terminal of ziconotide with N-terminal of a membrane penetrating peptide is suitable for intravenous or abdominal administration. In order to further investigate analgesic effects of different types of improved ziconotide, the present invention has designed and synthesized a variety of fusion polypeptides with different types and structures, including, a fusion polypeptide formed by directly linking C-terminal of ziconotide and N-terminal of a cell membrane penetrating peptide without a linker; a fusion polypeptide constructed using one or more glycines as linkers. Further, structural characterization of the above different types of fusion polypeptides, cell experiment, in vivo experiment, and side effect verification experiment are performed to illustrate effects of different types of improved ziconotide In order to better understand the technical solutions of the present invention, detailed descriptions are given below in conjunction with examples.

Example 1 Preparation of Different Types of Ziconotide Fusion Peptides

Four different types of fusion peptides were prepared and named as protected polypeptides MVIIA-a, MVIIA-b, MVIIA-c, and MVIIA-d. Meanwhile, ziconotide was prepared and named MVIIA as a control. F-moc automatic solid-phase synthesis method was used in this experiment with the specific steps of:

Synthesis of peptides: Protected peptides and their derivatives were assembled on the resin using model 433A automatic synthesizer (ABI, Foster City, CA). The peptide resin was incubated at room temperature in a suspension for 2.5 hours to remove protecting groups. The suspension system was composed of 10 ml TFA, 0.75 g phenol, 0.25 ml 1,2-ethanedithiol, 0.5 ml thioanisole and 0.5 ml water. (fluorenylmethoxycarbonyl (Fmoc), a common alkoxycarbonyl amino protecting group). The resin was separated from the peptide deprotection mixture by filtration. The crude polypeptide was precipitated in 150 ml of pre-cooled ether solution, and chromatographic purification was carried out on a Sephadex G-25 column with 10% glacial acetic acid as the eluent. Subsequently, the peptide-containing components were pooled and lyophilized, and the purity of the crude peptide was determined to be about 80% using high performance liquid chromatography.

Peptide folding: MVIIA comprised six cysteine residues to maintain its three disulfide bond structure. Folding under oxidative conditions could produce a variety of isomers. After screening for redox system, buffer, salt, concentration and temperature, two efficient folding conditions of MVIIA were selected: (a) 0.5 M NH4Ac buffer (pH 7.9), which contained 1 mM GSH, 0.1 mM GSSG, 1 mM EDTA, and 0.2 mg/mL MVIIA; (b) 0.5 M NH4Ac buffer, which contained 1 mM cysteine, 1 mM EDTA, and 0.2 mg/mL MVIIA. At 4° C., the linear polypeptide MVIIA was folded for 48-72 hours under the a condition and for 24-48 hours under the b condition.

Peptide purification and characterization: After the oxidation of MVIIA, the reaction mixture was acidified (pH <4.5) with acetic acid, and then filtered. The filtrate was directly loaded onto a Zorbax 21.2×250 mm C18 liquid chromatography column, which used a preparative high performance liquid chromatography pump (Waters 2000 series, Milford, MA). The C18 column was first pre-washed with buffer A (0.1% TFA in water), followed by linear gradient elution with 10-40% buffer B (0.1% TFA in acetonitrile) at a rate of 8 mL/min for 40 minutes. The obtained fraction was a concentrate containing 90% MVIIA, which was then further purified by semi-preparative reversed-phase high performance liquid chromatography equipped with a 9.4×250 mm Zorbax C18 liquid chromatography column. Finally, 20% acetic acid solution was used as eluent in a Sephadex G-25 chromatography column to convert the final product from the TFA salt solution to the acetate solution. The purity of the peptides was evaluated by analytical reversed-phase high performance liquid chromatography. For the evaluation, a linear gradient elution with 8-40% buffer B (0.1% TFA in acetonitrile) at a flow rate of 1 ml per minute for 25 minutes was performed by using a Zorbax C18 liquid chromatography column (4.6×250 mm). Finally, the purity of the final product (i.e., the peptide) was 98%.

Example 2: Chemical Properties and Structural Characterization of Different Types of Ziconotide Fusion Peptides 1. Chemical Properties of MVIIA and its Variants At 4° C., the linear peptide was treated with buffer for 24-48 hours, and then analyzed by high performance liquid chromatography. It was found that the folding of the linear peptide resulted in a major peak and several small peaks. The buffer system contained 1 mM glutathione, 0.1 mM oxidized glutathione, 1 mM EDTA, and 0.2 mg/mL linear peptide, at pH of 7.9. The main product was purified and evaluated by analytical reverse-phase high performance liquid chromatography, and the purity of the peptide was determined to be more than 98%. The determination was made with an Ultraflex III TOF/TOF mass spectrometer (Bruker). The prepared polypeptide sequences were shown in Table 1, and their one-step oxidation folding HPLC analysis profiles were shown in FIG. 1.

TABLE 1

Prepared peptide sequences

| Name | Sequence |
|---|---|
| MVIIA (SEQ ID NO. 1) | CKGKGAKCSRLMYDCCTGSCRSGKC |
| MVIIA-a (SEQ ID NO. 4) | CKGKGAKCSRLMYDCCTGSCRSGKCYGRKKRRQRRR |
| MVIIA-b (SEQ ID NO. 5) | CKGKGAKCSRLMYDCCTGSCRSGKCGYGRKKRRQRRR |
| MVIIA-c (SEQ ID NO. 3) | CKGKGAKCSRLMYDCCTGSCRSGKCGGYGRKKRRQRRR |
| MVIIA-d (SEQ ID NO. 6)) | CKGKGAKCSRLMYDCCTGSCRSGKCGGGYGRKKRRQRRR |

2. Circular Dichroism Spectroscopy

Peptides were dissolved in PBS (10 mM, pH=7.2) solution to final concentration of 35 μM. At room temperature, Chirascan Plus spectropolarimeter (Applied Photophysics Ltd., Leatherhead, Surrey, UK) instrument was used to detect the circular dichroism spectroscopy in the wavelength range of 190 nm to 260 nm. Detection parameters were set as follows: step resolution 1.0 nm; speed 20 nm/min, and cell path length of 1.0 mm.

Figure 2:
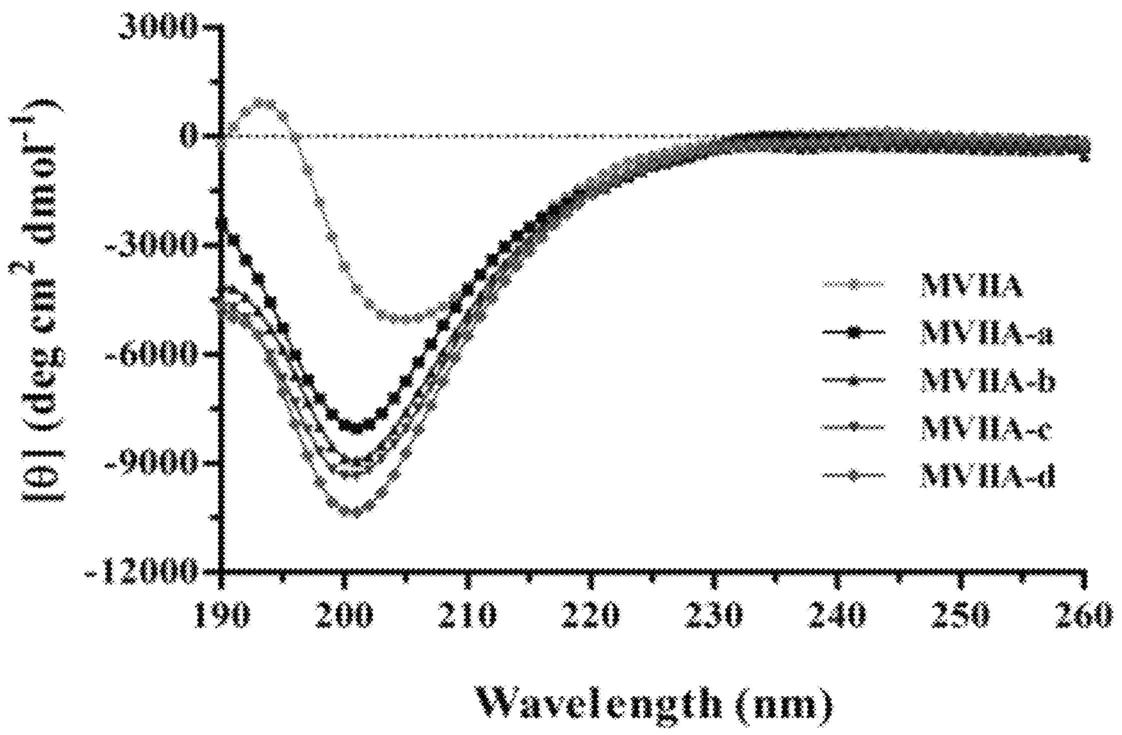
FIG. 2: circular dichroism spectra of MVIIA and MVIIA-a,b,c,d, wherein the final concentration of each peptide was 35 μmol/L dissolved in phosphate buffer (10 mM, pH=7.2) solution, respectively.

As shown in FIG. 2, MVIIA presented an obvious β-sheet structure between 195 nm-205 nm. We found that TAT variants showed a similar random coil structure with an obvious negative band at about 200 nm, suggesting the secondary structure of the peptides remained unchanged when the length of the linker between MVIIA and TAT sequence expanded. The molar ellipticity of TAT variants was deeper when linker expanded, suggesting that the expansion of the linker between MVIIA and TAT sequences helped to form a random coil. The exact molecular weights of the product peptides identified by the method of mass spectrometry (using Voyager MALDI-TOF spectrometer) was shown in Table 2, and the mass spectra of MVIIA and MVIIA-a, b, c, d were shown in FIG. 8-12. The bridging pattern of disulfide bonds was assigned based on the method that partially reduced cysteine coupling and amino acid silencing. The results of high performance liquid chromatogram and circular dichroism spectroscopy of the synthesized peptides and MVIIA standard product were consistent.

TABLE 2

Molecular weights of MVIIA and its variants

| Sample | Theoretical MW | Measured m/z | Difference between theoretical value and actual measured value |
|---|---|---|---|
| MVIIA | 2645.54 | 2639.0198 | 6.5202 |
| MVIIA-a | 4186.0784 | 4180.0108 | 6.0676 |
| MVIIA-b | 4243.0978 | 4237.0300 | 6.0678 |
| MVIIA-c | 4299.1353 | 4292.0362 | 7.0991 |
| MVIIA-d | 4356.1568 | 4351.0842 | 5.0726 |

HEK293T cells. 24 hours after transfection, the cells were seeded on glass slides and cultured in an incubator (37° C., 5% $CO_2$) for at least 6 hours, followed by electrophysiological recording.

This study was recorded in accordance with the method of cell voltage clamp recording in previously published research literature (F. Wang et al., 2016). Briefly, recording electrodes, with a resistance of ~3 MW, were filled with an internal solution. The internal solution contained the following: 135 mM CsCl, 10 mM NaCl, 10 mM HEPES, and 5 mM EGTA, and was adjusted to pH 7.2 with CsOH. The extracellular recording solution contained: 135 mM N-Methyl-D-glucamine, 10 mM $BaCl_2 \cdot 2H_2O$, 2 mM $MgCl_2 \cdot 6H_2O$ and 10 mM HEPES, with a final solution pH of 7.4. Acquired currents were recorded at room temperature (~22° C.) with a MultiClamp 700B amplifier (Molecular Devices, Sunnyvale, CA) and Clampex 10.3/Digidata1440A data acquisition system and digital-to-analog converter. Membrane currents were filtered at 2 kHz and sampled at 10 kHz. All data were analyzed with the data analysis system clampfit 10.3 software (Molecular Devices), presented as mean±S.E.M. Dose-response curves of toxin blocking N-type calcium ion current were obtained using GraphPad Prism (GraphPad Software, San Diego, CA) by plotting the inhibition of current amplitude as a function of drug concentration and were fitted using a hill equation.

Primary amino acid sequences and electrophysiological activities of MVIIA and its variants MVIIA-a, b, c, d were shown in Table 3.

TABLE 3

Primary amino acid sequences and electrophysiological activities of MVIIA and its variants

| Peptides | Primary amino acid sequences | $IC_{50}$ (μM) |
|---|---|---|
| MVIIA (SEQ ID NO: 1) | CKGKGAKCSRLMYDCCTGSCRSGKC | 0.0436 |
| L-MVIIA (SEQ ID NO: 7) | GGGGS-CKGKGAKCSRLMYDCCTGSCRSGKC | >10 |
| MVIIA-a (SEQ ID NO: 4) | CKGKGAKCSRLMYDCCTGSCRSGKC-YGRKKRRQRRR | 0.4127 |
| MVIIA-b (SEQ ID NO: 5) | CKGKGAKCSRLMYDCCTGSCRSGKC-G-YGRKKRRQRRR | 0.3788 |
| MVIIA-c (SEQ ID NO: 3) | CKGKGAKCSRLMYDCCTGSCRSGKC-GG-YGRKKRRQRRR | 0.2367 |
| MVIIA-d (SEQ ID NO: 6) | CKGKGAKCSRLMYDCCTGSCRSGKC-GGG-YGRKKRRQRRR | 0.3446 |

Figure 3:
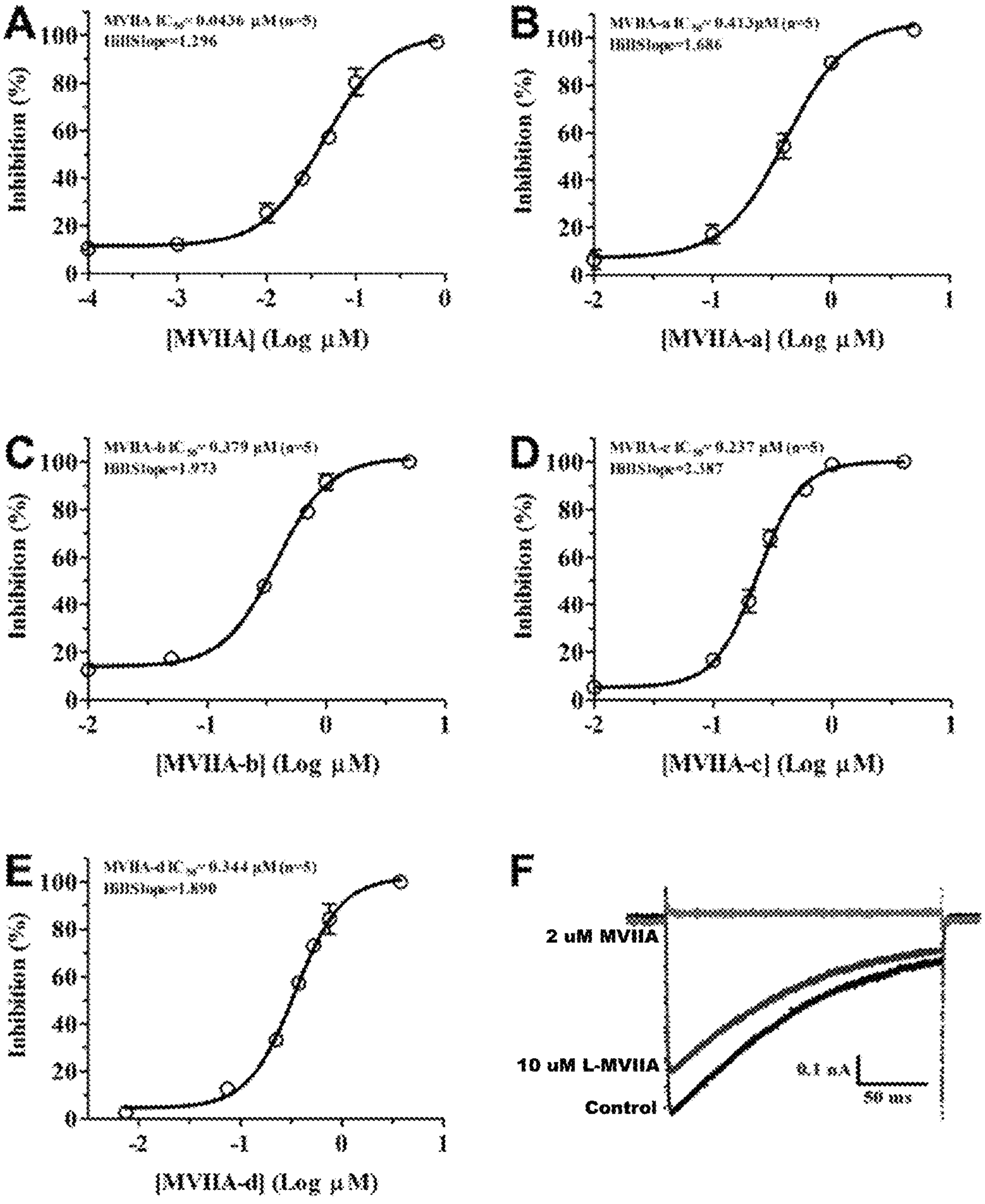
FIG. 3: inhibitory effects of MVIIA and MVIIA-a, b, c, d on CaV2.2 channel currents. The dose-response curve for MVIIA was shown in FIG. 3A, and the dose-response curve for MVIIA variants were shown in FIG. 3B-3E. Data of half inhibitory concentration and the slope value were shown in the figure, and data were presented as mean±S.E.M., with 5 mice in each group. As shown in FIG. F, superimposed traces of whole-cell calcium channel currents elicited by a voltage step from −80 mV to 10 mV at 10 μM L-MVIIA (blue) and 2 μM MVIIA (red); FIG. G was a summary table on the half inhibitory concentrations of MVIIA and its variants.

Example 3: Electrophysiological Experiment of Different Types of Ziconotide Fusion Peptides In order to further investigate electrophysiological effects and inhibitory effect on calcium (CaV2.2) channels of different types of modified ziconotide, the following experiments were carried out:

HEK293T cells (expressing SV40 large T antigen) were cultured in DMEM high glucose medium (Gibco) containing 10% fetal bovine serum, 1% penicillin and streptomycin, at the incubator environment of 37° C., 5% $CO_2$. Rat CaV2.2 channel $\alpha_{1B}$ splice variant e37a, auxiliary subunit $\alpha_2\delta_1$ and $\beta_3$ plasmids (Addgene plasmid #26569, #26575, #26574) were provided by Dr. Diane Lipscombe. Three plasmids (3 μg), 0.4 μg enhanced green fluorescent protein gene and liposomes were then transiently co-transfected into Inhibitory Effects on Calcium (CaV2.2) Channels Induced by MVIIA and its Variants It was well known that MVIIA was a selective CaV2.2 channel blocker. The inhibitory effect of 2 μM MVIIA on CaV2.2 channel was more than 90%. (F. Wang. 2016, and other articles) In this study, we recorded the peak $Ca^{2+}$ current (ICa) of CaV2.2 channels ($\alpha_{1B}$, $\alpha_2\delta_1$ and $\beta_3$) in the 293T cells. All currents were evoked by a 100 ms voltage step from −80 my to 10 my. MVIIA, MVIIA-a, MVIIA-b, MVIIA-c and MVIIA-d treatment at a concentration of 1 μM could reduce the peak $Ca^{2+}$ current by 98.24±0.708%, 89.45±0.752%, 91.70±1.477%, 98.81±0.427% and 84.26±3.127%, respectively. We found that MVIIA-c and MVIIA had similar ability in blocking CaV2.2 channels. L-MVIIA showed a significantly reduced ability in blocking Cav2.2, with reduced ICa amplitude of 23.28±3.347% at a concentration of 10 μM. The concentration-response relationship for MVIIA inhibition of CaV2.2 channel had a half inhibitory concentration of 0.0436 μM, which was almost 5-10 folds larger than that of TAT variants. The half inhibitory concentrations of TAT variants (MVIIA-a, MVIIA-b, MVIIA-c and MVIIA-d) were 0.413, 0.379, 0.237, and 0.345 μM, respectively, as shown in FIG. 3. These results suggested that MVIIA-a, MVIIA-b, MVIIA-c and MVIIA-d had a certain inhibitory effect on Cav2.2 channels, and the length of the linker sequence between MVIIA and TAT variants could affect the binding ability to Cav2.2 channels.

Example 4: Antinociceptive Effect In Vivo of Different Types of Ziconotide Fusion Peptides 1. Hot-Plate Pain Test 1.1 Test Method In this test, a total of nine groups of 6-8 mice were intracerebroventricularly administered MVIIA (0.11, 0.33 or 1.00 nmol/kg), or were tail intravenously administered MVIIA and MVIIA-a, MVIIA-b, MVIIA-c and MVIIA-d (0.33, 1.00 or 3.00 μmol/kg). Normal saline was administered in each routes as vehicle treated groups. The animals were placed on a hot plate with a constant temperature of 55±0.5° C. The latency time was recorded from the placement on the heated surface to the first licking of the hind paws or jumping as an index of pain threshold (Eddy and Leimbach, 1953). A cut-off time of 60 s was used: the mouse was taken out after 60s to avoid tissue damage. The latency time was measured before administration as the baseline latency; subsequently, the latency time was recorded at 0.5, 1, 2, 3, 4, 6, 8, 10, and 12 h after administration with MVIIA, MVIIA-c or Saline (intracerebroventricular or tail intravenous administration). Mice with a latency time less than 5 s or more than 20 s compared with the latency baseline time were subsequently eliminated to exclude hyposensitive or hypersensitive mice. The antinociceptive effect was expressed by latency time.

1.2 Comparison of Antinociceptive Ability

Figure 4:
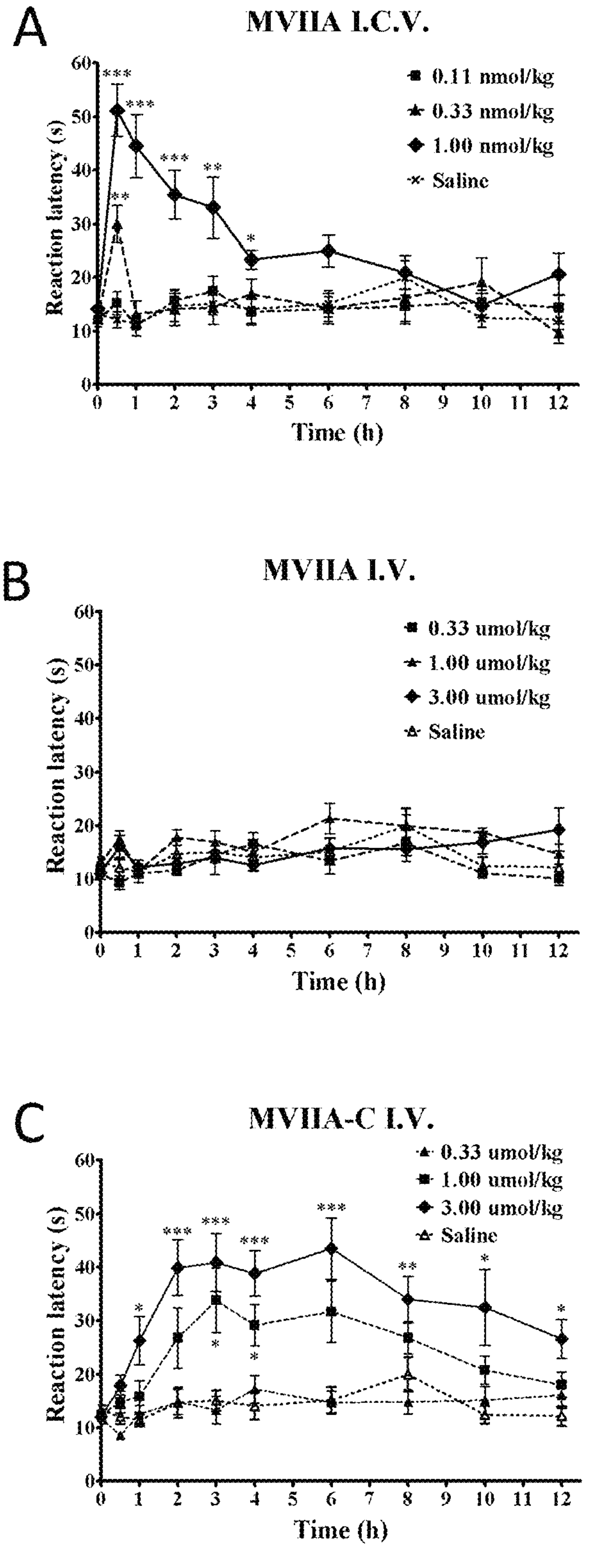
FIG. 4: comparison results of MVIIA and MVIIA-c on hot-plate pain. In vivo antinociceptive effects after intracerebroventricular administration of MVIIA (FIG. 4A), and tail intravenous administration of MVIIA (FIG. 4B) and MVIIA-c (FIG. 4C). The antinociceptive effect was expressed as reaction latency. Data were presented as mean±S.E.M., with 6-8 mice in each group. *$p<0.05$, $p<0.01$ and *$p<0.001$ indicated comparison with the normal saline group (data were analyzed by repeated multivariate analysis of variance and Duncan's multiple range test)

As shown in FIG. 4, MVIIA (0.11, 0.33, or 1.00 nmol/kg) exhibited a maximal effect 1 h after intracerebroventricular administration, and the effect substantially disappeared 4 h after administration (FIG. 4A). But MVIIA showed no effect when administered via tail intravenously administrations at multiple doses (FIG. 4B). MVIIA-c was the TAT variant of MVIIA that had the strongest inhibitory effect on CaV2.2 channel current. As shown in FIG. 4C, MVIIA-c exhibited a maximal effect at 3 hours after administration, with the maximal effect lasting about 4 hours and the effect disappearing within 12 hours.

Figure 5:
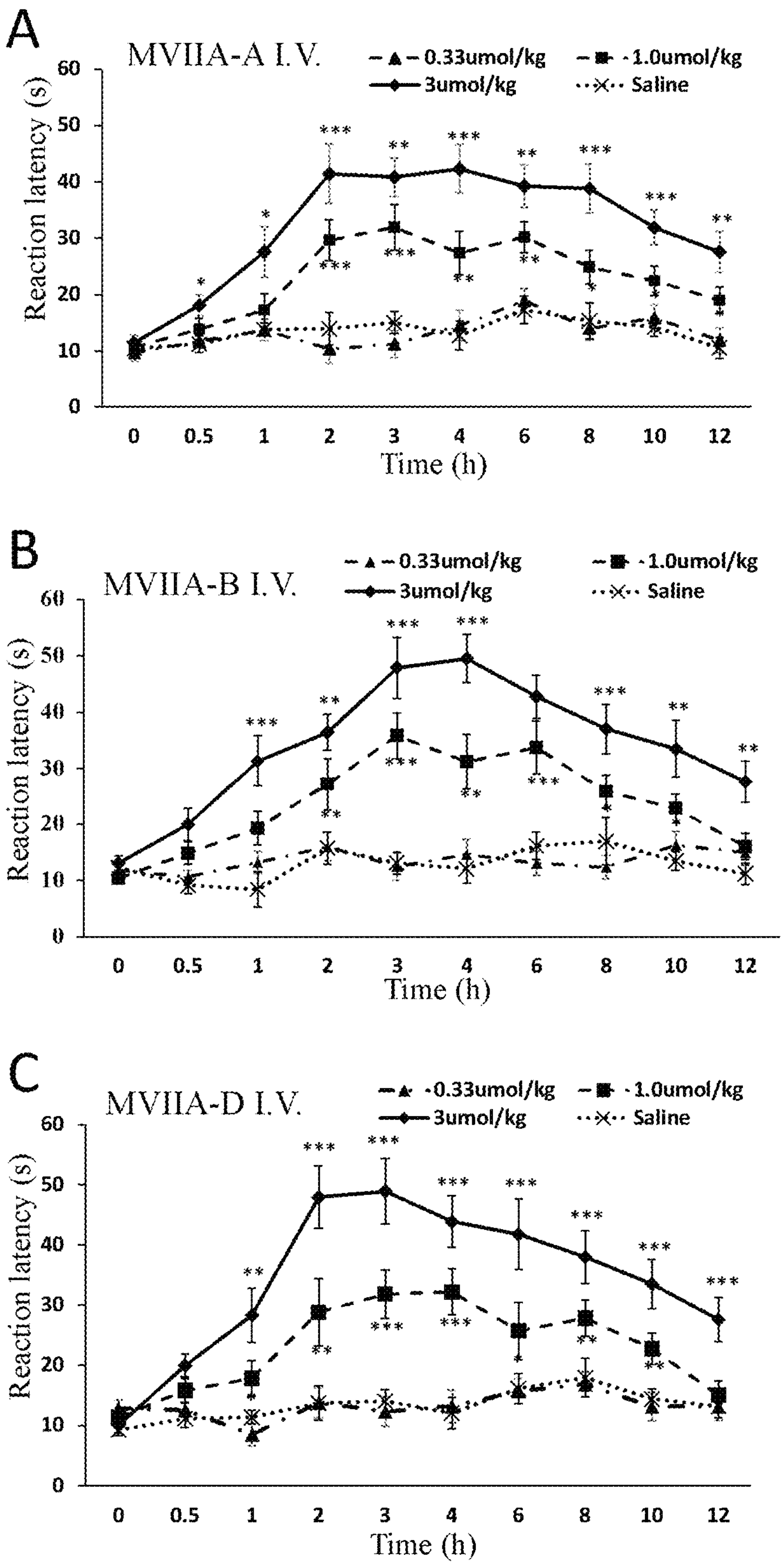
FIG. 5: results of MVIIA-a, b, d in hot-plate pain test.

As shown in FIG. 5, after tail intravenous injection of different doses of MVIIA-a, b, d (0.11 μmol/kg, 0.33 μmol/kg and 1.00 μmol/kg) for 1 hour, they all showed antinociceptive effects, and the strongest effect was presented at 2-3 hours, with the effect lasting about 4 hours. The effect was gradually decreased with time, and there was still a significant difference between the drug group and the saline group at 12 hours after the administration, with the effect lasting 12 hours.

2. Acetic Acid-Induced Writhing Test (Koster et al., 1959)

2.1 Test Method

Animals were treated with three dosages of MVIIA-a, b, c, d peptide group (0.6, 1.8 and 5.4 nmol/kg, low, middle and high dosages in the figure), saline control group (saline), or three dosages of positive reference drug group MVIIA (0.11, 0.33 and 1.00 nmol/kg), low, middle and high dosages in the figure). For the writhing test, mice were administered MVIIA (intracerebroventricularly) or MVIIA-a,b,c,d (intracerebroventricularly) 30 minutes before intraperitoneal injection of 1% acetic acid, followed by measuring their antinociceptive activities in vivo. To test the ability of MVIIA and MVIIA-a, b, c, d to penetrate the blood brain barrier, mice were administered MVIIA and MVIIA-a, b, c, d via tail vein 3 hours before intraperitoneal injection of 1% acetic acid. Saline group was used as a blank control group (intracerebroventricular or tail intravenous administration). The number of writhing responses was recorded from 5 minutes to 20 minutes after acetic acid injection (Galeotti et al., 2008). The recorded number of writhing movements was characterized by abdominal muscles contractions accompanied with stretching of hind limbs and elongation of the body.

2.2 Comparison of Antinociceptive Ability

Figure 6:
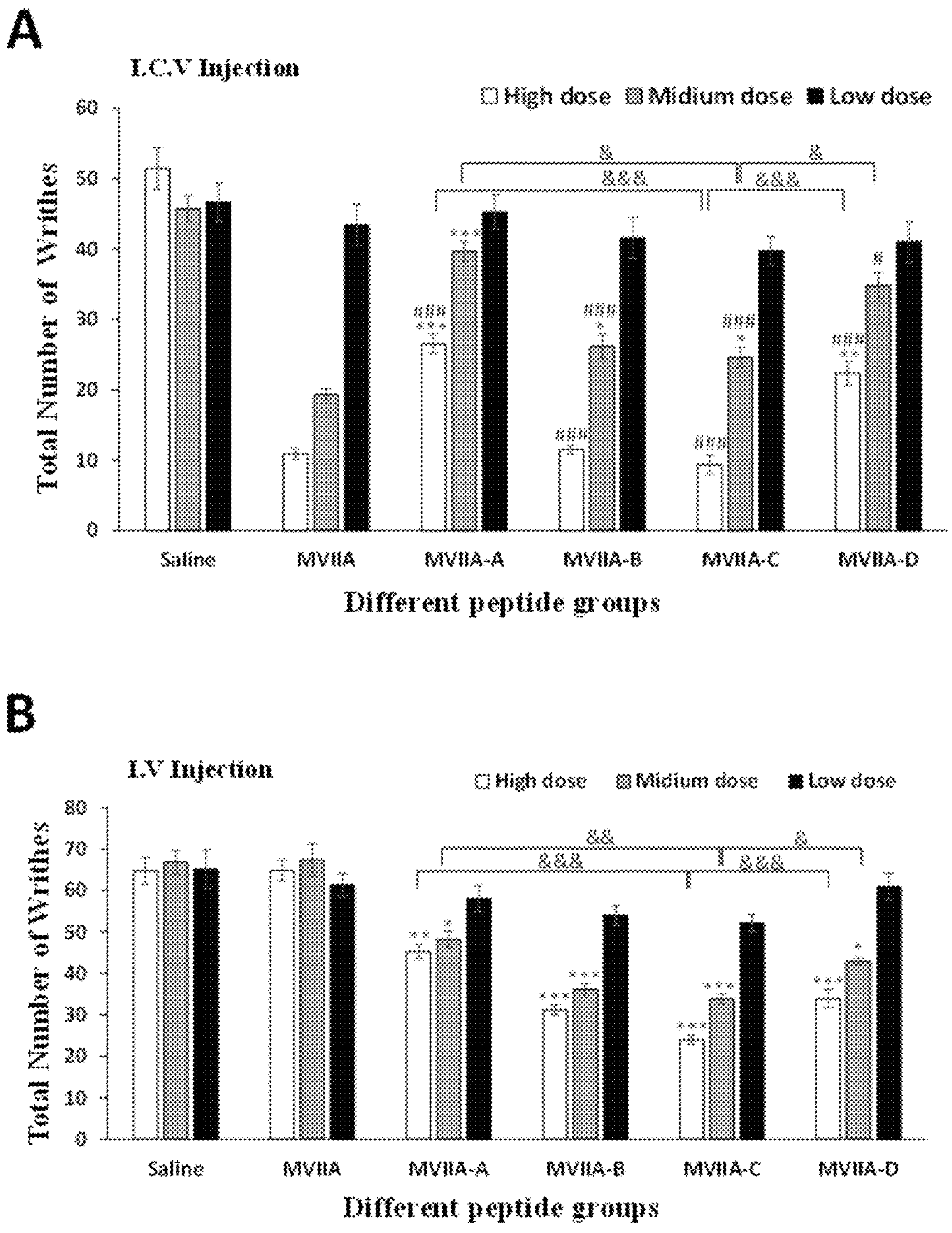
FIG. 6: antinociceptive effects of MVILA and MVIIA-a, b, d in acetic acid-induced writhing test. The number of writhing responses was counted from 5 minutes to 20 minutes after intraperitoneal injection of 1% acetic acid; as shown in FIG. A, comparison of effects of intraperitoneal injection of 1% acetic acid at 30 minutes after intracerebroventricular administration; as shown in FIG. B, comparison of effects of intraperitoneal injection of 1% acetic acid at 30 minutes after intravenous administration; #, compared with normal saline group; *, compared with MVIIA group; &, compared with MVIIA-C group; *, #, &, $p<0.05$; ***, ###, &&&, $p<0.001$. Data were presented as mean±S.E.M., with 9-11 mice in each group.

In the acetic acid-induced writhing test, animals were treated with three dosages of MVIIA-a, b, c, d peptide group (0.6, 1.8 and 5.4 nmol/kg, low, middle and high dosages in FIG. 6), saline control group (saline), three dosages of positive reference drug group MVIIA (0.11, 0.33 and 1.00 nmol/kg, low, middle and high dosages in FIG. 6). The numbers of writhing movements of each group at three different dosages after intravenous and intracerebroventricular administration. It was found that the MVIIA-a, b, c, d peptide group and the positive reference drug group MVIIA reduced the numbers of writhing movements induced by acetic acid in a dose-dependent manner. Under the conditions of intracerebroventricular administration, MVIIA, MVIIA-a, b, c, d reduced the number of writhing movements in mice to (relative to the saline group): MVIIA 8.97%, 53.37%, 76.88%; MVIIA-A, 2.94%, 13.36%, 48.35%; MVIIA-B, 10.82%, 42.79%, 77.60%; MVIIA-C, 14.75%, 39.53%, 81.77%; MVIIA-D, 12.08%, 23.95%, 56.54%. Under the conditions of intravenous administration, the positive reference drug MVIIA did not reduce the numbers of writhing movements in mice, and MVIIA-a, b, c, d reduced the numbers of writhing movements in mice to (relative to the saline group): MVIIA-a, 10.47%, 27.82%, 30.03%; MVIIA-b, 17.08%, 45.94%, 51.79%; MVIIA-c, 19.81%, 49.30%, 62.95%; MVIIA-d, 6.33%, 35.86%, 47.57%, as shown in FIG. 6.

In conclusion, from the above test results, it could be found that MVIIA-a, b, c, d peptides could show an antinociceptive effect after intravenous injection in a dose-dependent manner compared with MVIIA. In particular, in the case of middle and high dosages, MVIIA-a, b, c, d peptides could achieve good antinociceptive effects through intravenous injection and meet the needs of clinical application. Furthermore, compared with MVIIA, MVIIA-a, b, c, d showed effects up to 12 hours after intravenous injection and had a good sustained-release effect in vivo.

The above antinociceptive tests were analyzed using one-way ANOVA, two-way ANOVA with repeated measures, and, between groups, Duncan or Newman-Cole test. All data were presented as mean±S.D. or S.E.M. or 95% confidence interval. The differences with p values less than 0.05 were considered statistically significant.

Example 5: Side Effects Test of Different Types of Ziconotide Fusion Peptides

In order to further investigate the side effects of different types of modified ziconotide in vivo, the following test was carried out:

1. Test Method

Tremor time was regarded as a typical side-effect for ziconotide. The tremortime was the total time recorded for the rhythmic oscillatory movements of the mouse limbs, head, and trunk in a period of time. The mice were randomly divided into groups: MVIIA (0.9 nmol/kg) group, MVIIA-a,b,c,d (0.9 nmol/kg) group and a normal control group (6 μL, intracerebroventricular administration; n=12, half females and half males). 30 minutes and 120 minutes after administration, the dynamic video of the mice within 5 minutes was recorded by a digital camera, and the accumulative tremor time (s) in the period of 5 minutes was scored by a blinded observer.

The toxicology tests were analyzed using one-way ANOVA and Newman-Cole test. All data were presented as mean±S.D. or S.E.M. or 95% confidence interval. The differences with p values less than 0.05 were considered statistically significant.

2.1 Comparison of Side Effects

Figure 7:
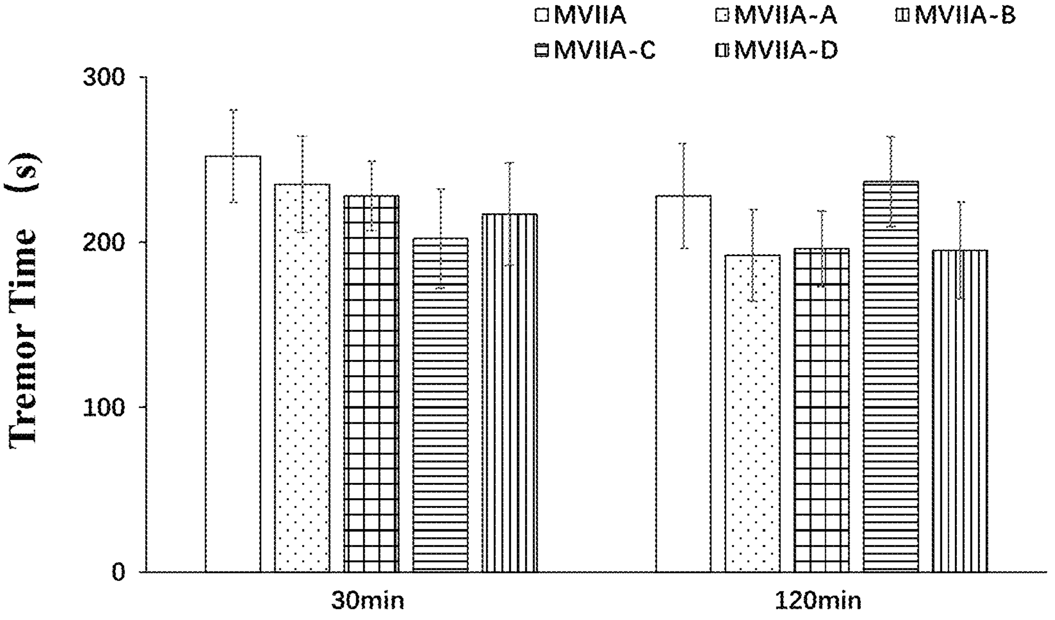
FIG. 7: effects of MVIIA and MVIIA-a, b, c, d on tremor time in mice. The peptides (0.9 nmol/kg) and normal saline were administered intracerebroventricularly to the mice in a volume of 6 μL. After 30 and 120 min, the accumulative tremor time (s) were recorded during a period of 5 min. Data were presented as mean±S.E.M. (n=12)
Figure 8:
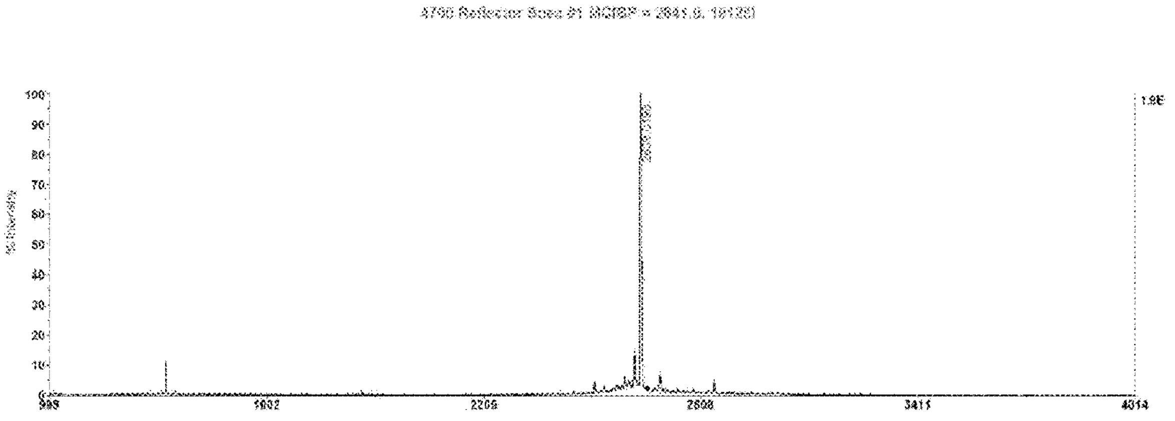
FIG. 8: mass spectrum for MVIIA.
Figure 9:
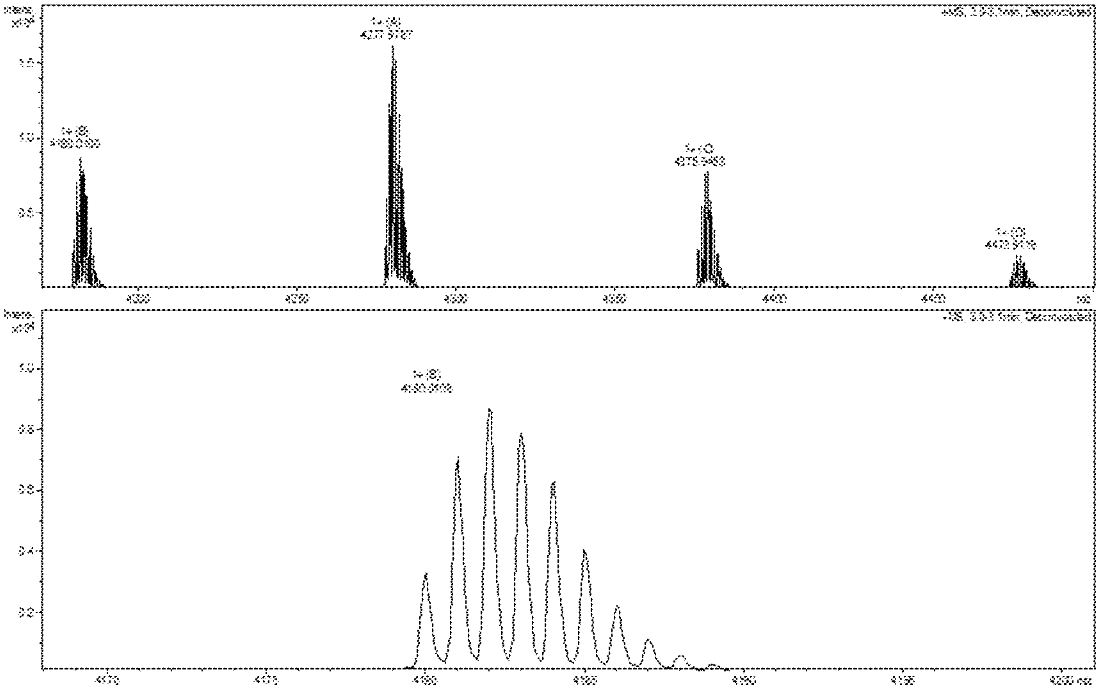
FIG. 9: mass spectrum for MVIIA-a.
Figure 10:
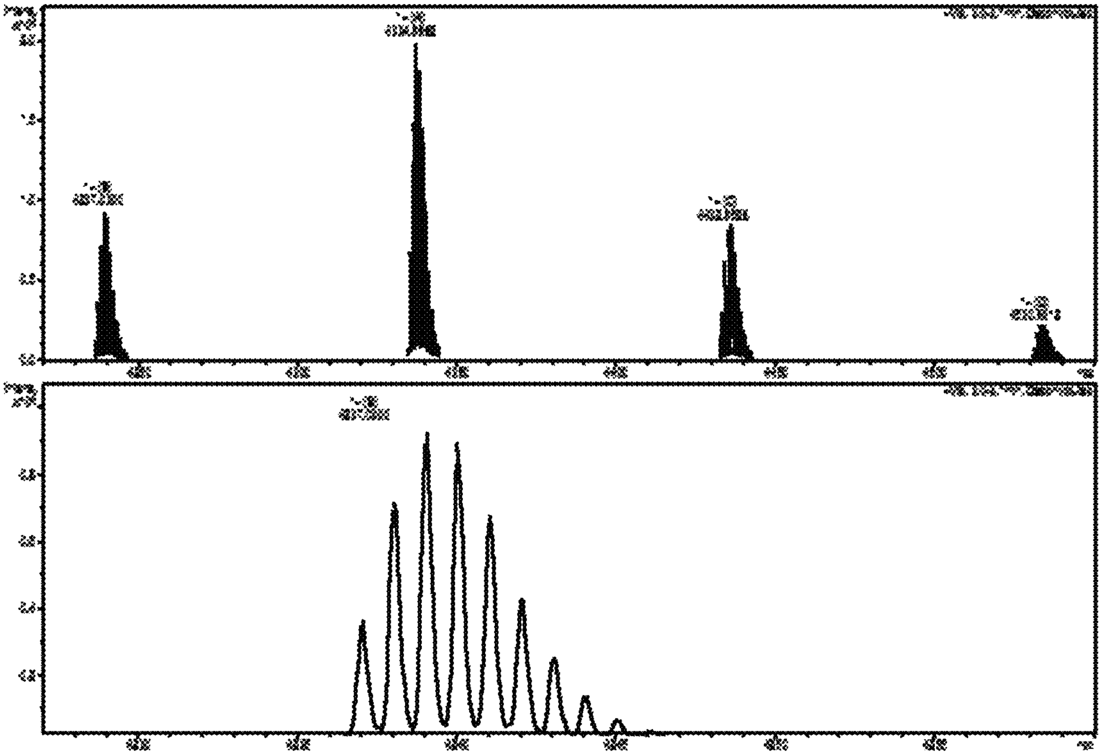
FIG. 10: mass spectrum for MVIIA-b.
Figure 11:
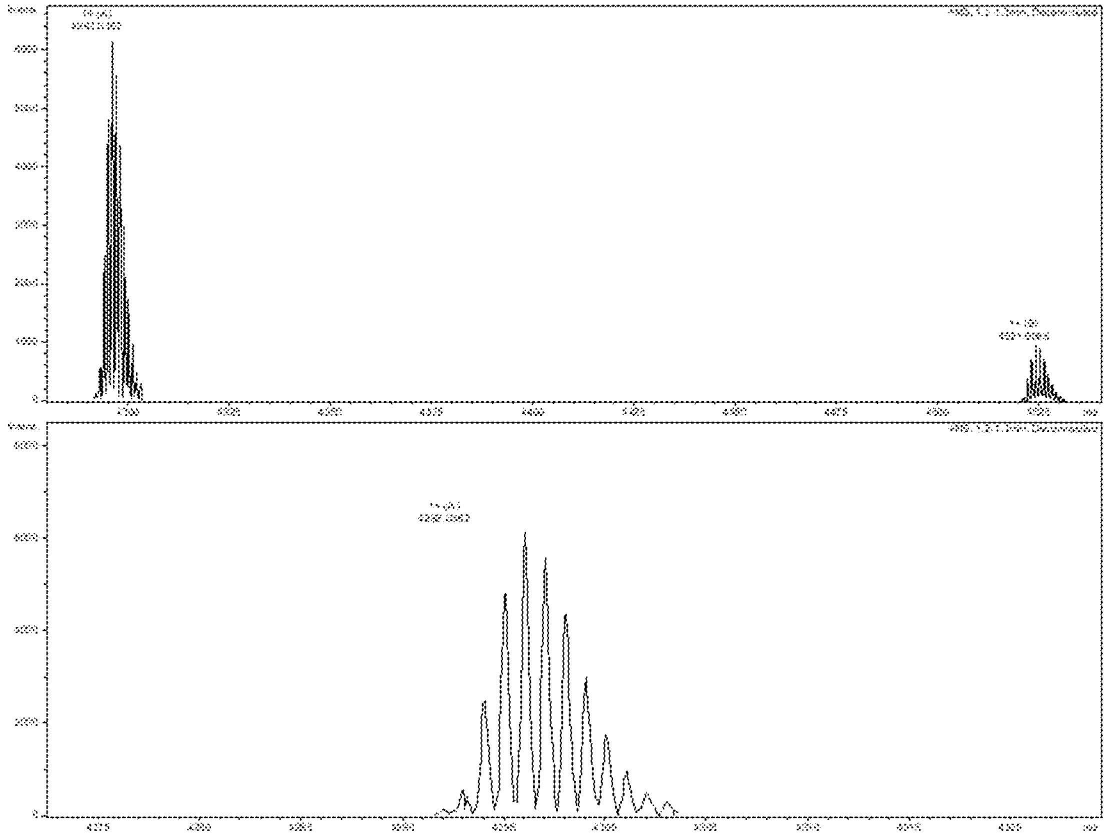
FIG. 11: mass spectrum for MVIIA-c.
Figure 12:
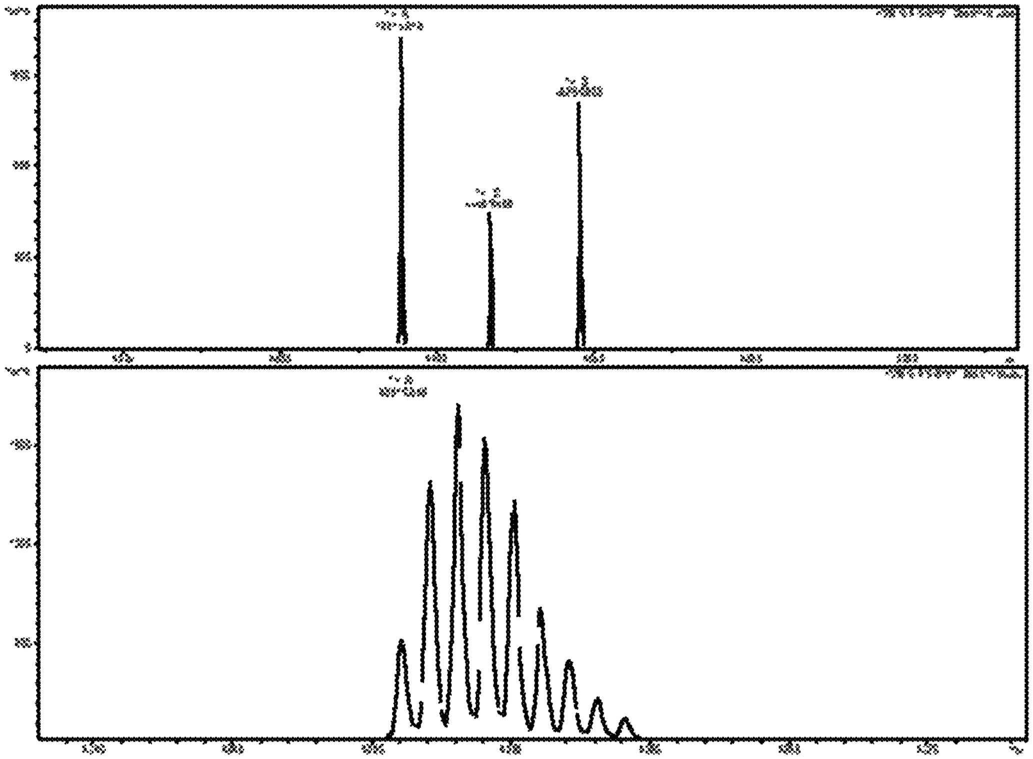
FIG. 12: mass spectrum for MVIIA-d.

As shown in FIG. 7, MVIIA induced more obvious tremor symptoms and longer tremor time 30 minutes after administration; compared with MVIIA, there were no significant differences in the tremor symptoms and longer tremor times induced by the peptides of each group 120 minutes after administration. It could be seen from the above results that there were no significant differences in side effects between MVIIA and MVIIA-a, b, c, d polypeptides. Moreover, at the beginning of administration, the side effects of MVIIA-a, b, c, d were lower than that of MVIIA. Therefore, the MVIIA-a, b, c, d polypeptides of the present application had less toxic and side effects.

Example 6: Comparison of Antinociceptive Tests for MVII-A Intracerebroventricular Administration and MVIIA-a, b, c, d Intranasal Administration 1.1 Test Method for Hot-Plate Pain Test method for hot-plate pain was as described above. In this test, a total of nine groups of 10 mice were intracerebroventricularly administered MVIIA (1.00 nmol/kg, 5 μl/10 g) as a positive control group (in the test, it was found that MVIIA intranasal administration had no effect), and the nasal cavity was administered normal saline (saline, 2 μl/10 g), MVIIA-C(3.3, 6.6 or 9.9 nmol/kg, 2 μl/10 g), respectively. The saline group served as the blank control group. The latency time was recorded 0.5, 1, 2, 3, 4, 6, 8, 10 h after intracerebroventricular administration of MVIIA, nasal administration of MVIIA-c and Saline. Mice with a latency time less than 5 s or more than 20 s compared with the latency baseline time were subsequently eliminated to exclude hyposensitive or hypersensitive mice.

The antinociceptive effect was expressed as a percentage of the maximum possible effect (% MPE), and finally calculated by the following equation: % MPE=$(T_1-T_0)\times 100/(T_2-T_0)$ Wherein $T_0$ and $T_1$ respectively represented the latency time before and after administration, and $T_2$ was the limit time of each test.

1.2 Test Results

Figure 13:
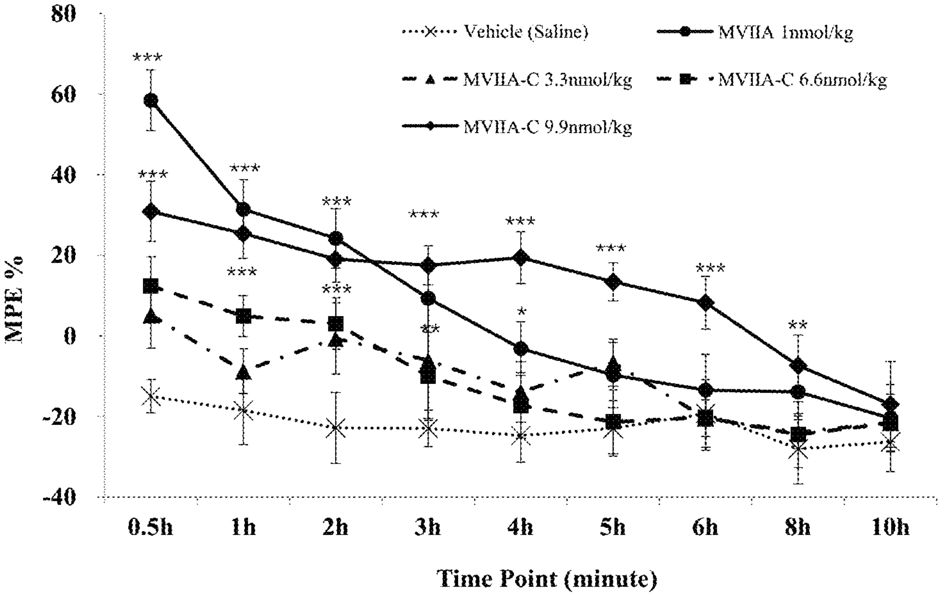
FIG. 13: antinociceptive abilities of MVIIA and different doses of MVIIA-c after nasal administration.

FIG. 13 showed the antinociceptive ability of MVIIA and different dosages of MVIIA-c after nasal administration. FIG. 13 showed antinociceptive effects of MVIIA intracerebroventricular and MVIIA-c nasal administration in the hot plate pain test. After intracerebroventricular administration of MVIIA (1.00 nmol/kg), the effect lasted 4 hours. MVIIA-C (3.3, 6.6, 9.9 nmol/kg) showed immediate effect after nasal administration. The high-dose MVIIA-C lasted a long time, and it was still significantly different from the saline group at 8 hours, with the effect disappearing after 10 hours. *p<0.05, p<0.01 and *p<0.001 indicated comparison with the saline group.

1.3 Antinociceptive Test for MVIIA-a,b,d Intranasal Administration

Figure 14:
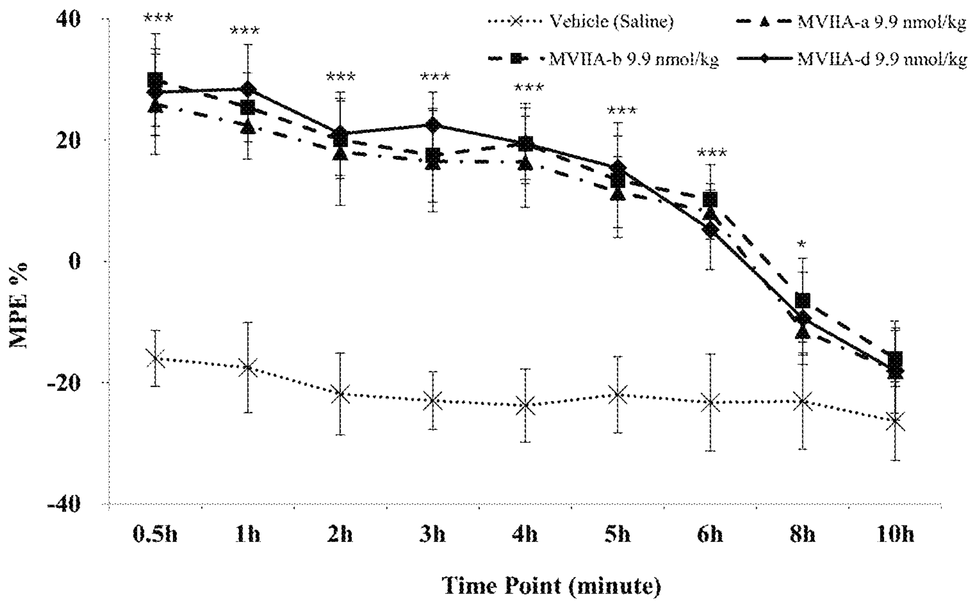
FIG. 14: antinociceptive abilities of MVIIA-a, b, d during nasal administration in the hot-plate pain test.

FIG. 14 showed the antinociceptive effects of MVIIA-a, b, d intranasal administration in hot-plate pain test. Similar to MVIIA-C, MVIIA-a,b,d (9.9 nmol/kg) showed immediate effect after nasal administration, and MVII-b was still significantly different from the saline group at 8 hours, with the effect disappearing after 10 hours. *p<0.05, ***p<0.001 indicated comparison with the saline group.

In the above, the present invention has been described in detail with general instructions and specific embodiments, but on the basis of the present invention, some modifications or improvements can be made, which is obvious to those skilled in the art. Therefore, these modifications or improvements made without departing from the spirit of the present invention fall within the scope of the present invention.

The invention claimed is:

1. A polypeptide comprising ziconotide, wherein the polypeptide is able to cross blood-brain barrier, wherein the polypeptide consists of ziconotide and a cell membrane penetrating peptide, or the polypeptide consists of ziconotide, a cell membrane penetrating peptide and a linker, wherein C-terminal of the ziconotide is linked to N-terminal of a cell membrane penetrating peptide adjacently or via a linker, and wherein the ziconotide has amino acids shown in SEQ ID NO.1, or the ziconotide is a variant of the amino acids shown in SEQ ID NO.1 with less than 4 amino acid deletions, mutations or insertions.

2. The polypeptide according to claim 1, wherein the linker is one, two or three glycines.

3. The polypeptide according to claim 1, wherein the cell membrane penetrating peptide is selected from: Penetratin, TAT peptide, Pep-1 peptide, $S4_{13}$-PV, Magainin 2 or Buforin 2.

4. The polypeptide according to claim 3, wherein the TAT peptide has amino acids shown in SEQ ID NO.2, or the TAT peptide is a variant of the amino acids shown in SEQ ID NO.2 with less than 4 amino acid deletions, mutations or insertions.

5. The polypeptide according to claim 1, wherein the amino acid sequence of the polypeptide is shown in anyone of SEQ ID NO.3-6.

6. A pharmaceutical composition comprising the polypeptide of claim 1 and an acceptable carrier.

7. The pharmaceutical composition according to claim 6, wherein the pharmaceutical composition is to be administered intravenously, intraperitoneally or nasally, and the pharmaceutical composition is in a dosage form for intravenous, intraperitoneal or nasal administration.

8. A method for preparing a polypeptide, the method comprises synthesizing a polypeptide comprising ziconotide, wherein the polypeptide is able to cross blood-brain barrier, wherein the polypeptide consists of ziconotide and a cell membrane penetrating peptide, or the polypeptide consists of ziconotide, a cell membrane penetrating peptide and a linker, wherein C-terminal of the ziconotide is linked to N-terminal of a cell membrane penetrating peptide adjacently or via a linker, and wherein the ziconotide has amino acids shown in SEQ ID NO.1, or the ziconotide is a variant of the amino acids shown in SEQ ID NO.1 with less than 4 amino acid deletions, mutations or insertions.

9. The pharmaceutical composition according to claim 6, wherein the amino acid sequence of the polypeptide is shown in anyone of SEQ ID NO.3-6.

10. The method according to claim 8, wherein the amino acid sequence of the polypeptide is shown in anyone of SEQ ID NO.3-6.

11. A method of treating pain or pain-related diseases, comprising:

administering the pharmaceutical composition according to claim 6 to a subject in need thereof.

12. The method according to claim 11, wherein the pharmaceutical composition is administered intravenously, intraperitoneally or nasally.

13. The method according to claim 11, wherein the amino acid sequence of the polypeptide is shown in anyone of SEQ ID NO.3-6.

* * * * *

SEQUENCE LISTING

```
<160> NUMBER OF SEQ ID NOS: 7

<210> SEQ ID NO 1
<211> LENGTH: 25
<212> TYPE: PRT
<213> ORGANISM: Artificial Sequence
<220> FEATURE:
<223> OTHER INFORMATION: ziconotide

<400> SEQUENCE: 1

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25


<210> SEQ ID NO 2
<211> LENGTH: 11
<212> TYPE: PRT
<213> ORGANISM: Artificial Sequence
```

-continued

<220> FEATURE:
<223> OTHER INFORMATION: TAT peptide

<400> SEQUENCE: 2

```
Tyr Gly Arg Lys Lys Arg Arg Gln Arg Arg Arg
1               5                   10
```

<210> SEQ ID NO 3
<211> LENGTH: 38
<212> TYPE: PRT
<213> ORGANISM: Artificial Sequence
<220> FEATURE:
<223> OTHER INFORMATION: fusion polypeptide of ziconotide and TAT peptide

<400> SEQUENCE: 3

```
Cys Lys Gly Lys Gly Ala Lys Cys Ser Arg Leu Met Tyr Asp Cys Cys
1               5                   10                  15

Thr Gly Ser Cys Arg Ser Gly Lys Cys Gly Gly Tyr Gly Arg Lys Lys
            20                  25                  30

Arg Arg Gln Arg Arg Arg
        35
```

<210> SEQ ID NO 4
<211> LENGTH: 36
<212> TYPE: PRT
<213> ORGANISM: Artificial Sequence
<220> FEATURE:
<223> OTHER INFORMATION: fusion polypeptide of ziconotide and TAT peptide

<400> SEQUENCE: 4

```
Cys Lys Gly Lys Gly Ala Lys Cys Ser Arg Leu Met Tyr Asp Cys Cys
1               5                   10                  15

Thr Gly Ser Cys Arg Ser Gly Lys Cys Tyr Gly Arg Lys Lys Arg Arg
            20                  25                  30

Gln Arg Arg Arg
        35
```

<210> SEQ ID NO 5
<211> LENGTH: 37
<212> TYPE: PRT
<213> ORGANISM: Artificial Sequence
<220> FEATURE:
<223> OTHER INFORMATION: fusion polypeptide of ziconotide and TAT peptide

<400> SEQUENCE: 5

```
Cys Lys Gly Lys Gly Ala Lys Cys Ser Arg Leu Met Tyr Asp Cys Cys
1               5                   10                  15

Thr Gly Ser Cys Arg Ser Gly Lys Cys Gly Tyr Gly Arg Lys Lys Arg
            20                  25                  30

Arg Gln Arg Arg Arg
        35
```

<210> SEQ ID NO 6
<211> LENGTH: 39
<212> TYPE: PRT
<213> ORGANISM: Artificial Sequence
<220> FEATURE:
<223> OTHER INFORMATION: fusion polypeptide of ziconotide and TAT peptide

<400> SEQUENCE: 6

-continued

```
Cys Lys Gly Lys Gly Ala Lys Cys Ser Arg Leu Met Tyr Asp Cys Cys
1               5                   10                  15

Thr Gly Ser Cys Arg Ser Gly Lys Cys Gly Gly Gly Tyr Gly Arg Lys
            20                  25                  30

Lys Arg Arg Gln Arg Arg Arg
        35


<210> SEQ ID NO 7
<211> LENGTH: 30
<212> TYPE: PRT
<213> ORGANISM: Artificial Sequence
<220> FEATURE:
<223> OTHER INFORMATION: fusion polypeptide of GGGGS and ziconotide

<400> SEQUENCE: 7

Gly Gly Gly Gly Ser Cys Lys Gly Lys Gly Ala Lys Cys Ser Arg Leu
1               5                   10                  15

Met Tyr Asp Cys Cys Thr Gly Ser Cys Arg Ser Gly Lys Cys
            20                  25                  30
```